United States Patent [19]

Rapoport

[11] Patent Number: 5,335,654

[45] Date of Patent: Aug. 9, 1994

[54] METHOD AND APPARATUS FOR CONTINUOUS ADJUSTMENT OF POSITIVE AIRWAY PRESSURE FOR TREATING OBSTRUCTIVE SLEEP APNEA

[75] Inventor: David M. Rapoport, New York, N.Y.

[73] Assignee: New York University, New York, N.Y.

[21] Appl. No.: 879,578

[22] Filed: May 7, 1992

[51] Int. Cl.$^5$ .............................................. A61M 16/00
[52] U.S. Cl. ........................... 128/204.23; 128/204.21; 128/207.18; 128/716; 128/725
[58] Field of Search ................ 128/204.18, 204.21, 128/204.23, 204.26, 205.18, 207.18, 716, 717, 718, 719, 720, 721, 722, 723, 724, 725, 726

[56] References Cited

U.S. PATENT DOCUMENTS

| | | | |
|---|---|---|---|
| 4,077,404 | 3/1978 | Elam | 128/204.28 |
| 4,365,636 | 12/1982 | Barker | 128/716 |
| 4,440,177 | 4/1984 | Anderson | 128/719 |
| 4,655,213 | 4/1987 | Rapoport et al. | 128/205.25 |
| 4,723,543 | 2/1988 | Beran | 128/207.14 |
| 5,065,756 | 11/1991 | Rapoport | 128/204.18 |
| 5,107,831 | 4/1992 | Halpern | 128/204.26 |
| 5,134,995 | 8/1992 | Gruenke et al. | 128/204.23 |
| 5,148,802 | 9/1992 | Sanders et al. | 128/204.18 |
| 5,199,424 | 4/1993 | Sullivan et al. | 128/204.18 |
| 5,203,343 | 4/1993 | Axe et al. | 128/725 |

FOREIGN PATENT DOCUMENTS 9106832  5/1991 World Int. Prop. O. ...... 128/204.22

OTHER PUBLICATIONS

"Ventilators", DuBois, CV Mosby Co., 1986, pp. 107–117.

"Digital Computation & Numerical Methods", Southworth, McGraw-Hill Co., 1965, pp. 6–10.

"Sleep Apnea-Diagnosis and Treatment", Topics in Primary Care Medicine, The Western Journal of Medicine, Aug. 1986; 145:248–250.

Sleep and Respiration, pp. 261–271, 1990 Wiley-Liss. Inc. Remmers J. E., Launois S. Feroah, T, Whitelaw Wash.

"Unattended CPAP Titration: Toward A Smart Machine", C. Guilleminault et al., Sleep Research 21, 1992, p. 342.

"Development And Application Of An Automatic Nasal CPAP Calibration Procedure For Use In The Unsupervised Home Environment", L. E. Miles et al., Sleep Research 21, 1992, p. 352.

"Reversal of Obstructive Sleep Apnea by Continuous Positive Airway Pressure Applied Through the Nares", Sullivan et al., Lancet, 1981, 1.862–865.

"Reversal of the 'Pickwickian Syndrome' By Long-Term Use of Nocturnal Nasal-Airway Pressure"; Rapoport et al., New England Journal of Medicine, Oct. 7, 1982.

"Induction of upper airway occlusion in sleeping individuals with subatmospheric nasal pressure", Schwartz et al., Journal of Applied Physiology, 1988, 64, pp. 535–542.

"Therapeutic Options For Obstructive Sleep Apnea" Garay, Respiratory Management, Jul./Aug., 1987, pp. 11–15.

"Techniques For Administering Nasal CPAP", Rapoport, Respiratory Management, Jul./Aug. 1987, pp. 18–21.

*Primary Examiner*—Edgar S. Burr
*Assistant Examiner*—Eric P. Raciti
*Attorney, Agent, or Firm*—Fulwider, Patton, Lee & Utecht

[57] ABSTRACT

In the treatment of obstructive sleep apnea, a CPAP flow generator is employed to direct air to a nasal mask fitted to a patient. The airflow from the generator is monitored, and the flow and/or pressure is increased when the waveform of the airflow exhibits characteristics corresponding to flow limitation. The generator may be controlled to repetitively test for waveform variations, in order to adjust the CPAP flow to the minimum level the does not produce flow limitation.

13 Claims, 5 Drawing Sheets

AIRFLOW TO AND
FROM CPAP GENERATOR

AIRFLOW TO AND
FROM CPAP GENERATOR

AIRFLOW TO AND
FROM CPAP GENERATOR

AIRFLOW TO AND
FROM CPAP GENERATOR

AIRFLOW TO AND
FROM CPAP GENERATOR

METHOD AND APPARATUS FOR CONTINUOUS ADJUSTMENT OF POSITIVE AIRWAY PRESSURE FOR TREATING OBSTRUCTIVE SLEEP APNEA

FIELD OF THE INVENTION

This invention relates to a method and apparatus for adjusting the positive airway pressure of a patient to have an optimum (e.g. minimum) value, in the treatment of obstructive sleep apnea.

BACKGROUND OF THE INVENTION

Obstructive sleep apnea syndrome (OSAS) is a well recognized disorder which may affect as much as 1-5% of the adult population. It is one of the most common causes of excessive daytime somnolence, and it is the single most frequent reason for referral to sleep disorder clinics.

The syndrome is characterized by the intermittent obstruction of the upper airway which occurs during sleep. The obstruction results in a spectrum of respiratory disturbances ranging from the total absence of airflow (apnea) to significant obstruction with or without reduced airflow (hypopnea and snoring), despite continued respiratory efforts. The morbidity of the syndrome arises from hypoxemia, hypercapnia, bradycardia and sleep disruption associated with the apneas and arousals from sleep. OSAS is most frequent in obses males, and is associated with all conditions in which there is anatomic or functional narrowing of the upper airway, as in heavy snoring.

The pathophysiology of OSAS is not fully worked out. However, it is now well recognized that obstruction of the upper airway during sleep is in part due to the collapsible behavior of the supraglottic segment during the negative intraluminal pressure generated by inspiratory effort. Thus, the human upper airway during sleep behaves as a Starling resistor, which is defined by the property that the flow is limited to a fixed value irrespective of the driving (inspiratory) pressure. Partial or complete airway collapse can then occur associated with the loss of airway tone which is characteristic of the onset of sleep and may be exaggerated in OSAS.

Since 1981, continuous positive airway pressure applied by a tight fitting nasal mask worn during sleep has evolved as the most effective treatment for this disorder, and is now the standard of care. The availability of this non-invasive form of therapy has resulted in extensive publicity for apnea and the appearance of large numbers of patients who previously may have avoided the medical establishment because of the fear of tracheostomy. Increasing the comfort of the system, which is partially determined by minimizing the necessary nasal pressure, has been a major goal of research aimed at improving patient compliance with therapy. Various systems for the treatment of obstructive sleep apnea are disclosed, for example, in "Reversal of Obstructive Sleep Apnea by Continuous Positive Airway Pressure Applied Through The Nares", Sullivan et al, Lancet, 1981, 1:862-865; and "Reversal Of The 'Pickwickian Syndrome' By Long-Term Use of Nocturnal Nasal-Airway Pressure"; Rapoport et al, New England Journal of Medicine, Oct. 7, 1982.

The article "Induction of upper airway occlusion in sleeping individuals with subatmospheric nasal pressure", Schwartz et al, Journal of Applied Physiology, 1988, 64, pp 535-542, also discusses various polysomnographic techniques.

Despite its success, limitations to the use of nasal CPAP exist. These mostly take the form of discomfort from the mask and the nasal pressure required to obliterate the apneas. Systems for minimizing the discomfort from the mask are disclosed, for example, in U.S. Pat. Nos. 4,655,213, Rapport et al, and 5,065,756, Rapoport, as well as in "Therapeutic Options For Obstructive Sleep Apnea", Garay, Respiratory Management, July/August, 1987, pp 11-15; and "Techniques For Administering Nasal CPAP", Rapoport, Respiratory Management, July/August 1987, pp 18-21. Minimizing the necessary pressure remains a goal of the preliminary testing of a patient in the sleep laboratory. However, it has been shown that this pressure varies throughout the night with sleep stage and body position. Furthermore, the therapeutic pressure may both rise or fall with time in patients with changing anatomy (Nasal congestion/polyps), change in weight, changing medication or with alcohol use. Because of this, most sleep laboratories currently prescribe the setting for home use of nasal CPAP pressure based upon the single highest value of pressures needed to obliterate apneas during a night of monitoring in the sleep laboratory. Retesting is often necessary if the patient complains of incomplete resolution of daytime sleepiness, and may reveal a change in the required pressure.

SUMMARY OF THE INVENTION

The invention is therefore directed to a method and apparatus for minimizing the CPAP pressure, in a system for the treatment of obstructive sleep apnea, without causing limitation of airflow to the patient by partial airway obstruction to occur.

Briefly stated an apparatus for the treatment of obstructive sleep apnea is provided, comprising a source of air, and means for directing an air flow from said source to a patient. This part of the system may be of the type disclosed, for example, in U.S. Pat. No. 5,065,756. In accordance with the invention, means are provided for sensing the waveform of said airflow, to detect deviations therein that correspond to flow limitation in the air supplied to the patient. Such deviations may be, for example, deviations from a substantially sinusoidal waveform, flattening, or the presence of plateaus, in the portions of the waveform corresponding to inspiration of the patient. In response to such variations in said airflow, the system of the invention increases the airflow to the patient.

The system may be provided with a program that periodically decreases the airflow in the absence of detection of airflow limitation, and that periodically increases the airflow in the presence of detection of the airflow limitation.

In accordance with the method of the invention, the airflow to the patient is increased in response to the detection of waveform portions corresponding to flow limitations. The increases may be effected periodically. Similarly, the flow may be periodically decreased in the absence of such flow limitation.

BRIEF DESCRIPTION OF THE DRAWING

In order that the invention may be more clearly understood, it will now be disclosed in greater detail with reference to the accompanying drawing, wherein.

DETAILED DISCLOSURE OF THE INVENTION

FIGS. 1-5 illustrate the waveforms of flow from a CPAP generator, obtained during the testing of a patient, in sleep studies. In these tests, the patient was wearing a CPAP mask connected to an air source, in the manner illustrated in U.S. Pat. No. 5,065,765. Each of these tests illustrate an epoch of 30 seconds, with the vertical lines depicting seconds during the tests. FIGS. 1-5 depict separate sweeps that were taken from 1 to 2 minutes apart, and with different pressures from the source of air.

Figure 1:
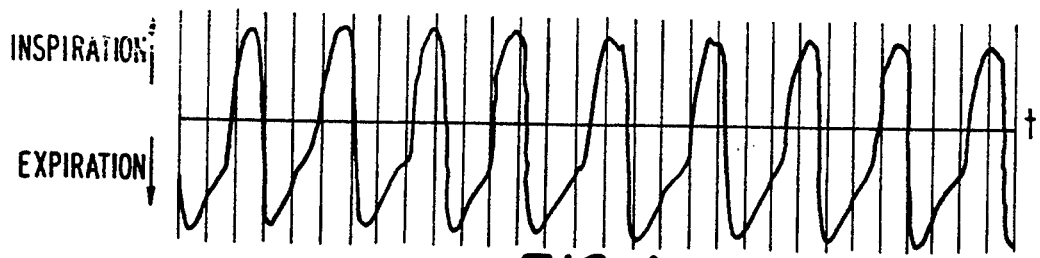
FIG. 1 is the waveform of the airflow of a 30 second epoch to a sleeping patient from a CPAP generator, with a CPAP pressure of 10 cm H₂O.

FIG. 1 illustrates a "normal" waveform, in this instance with a CPAP pressure of 10 cm H₂O. This pressure was identified as corresponding to obstruction free respiration. It is noted that this waveform, at least in the inspiration periods, is substantially sinusoidal.

Figure 2:
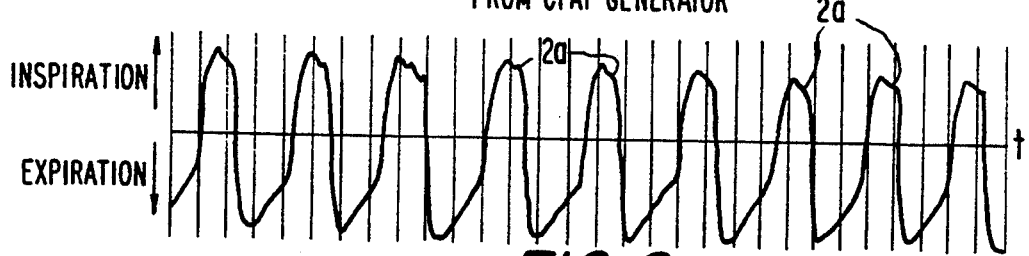
FIG. 2 is the waveform of the airflow of a 30 second epoch to the sleeping patient of FIG. 1, from a CPAP generator, with a CPAP pressure of 8 cm H₂O.
Figure 3:
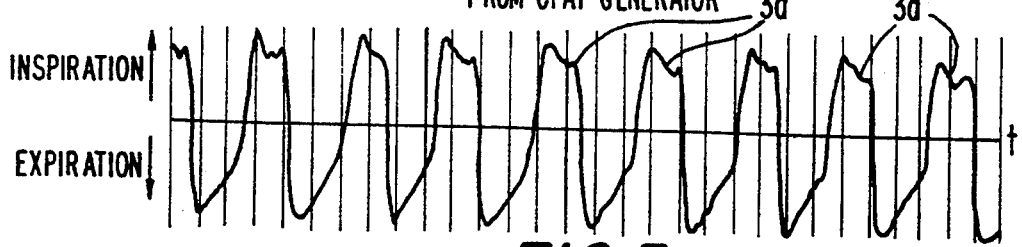
FIG. 3 is the waveform of the airflow of a 30 second epoch to the sleeping patient of FIG. 1, from a CPAP generator, with a CPAP pressure of 6 cm H₂O.
Figure 4:
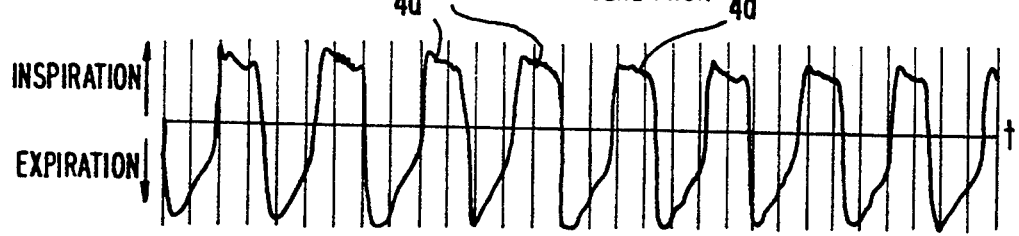
FIG. 4 is the waveform of the airflow of a 30 second epoch to the sleeping patient of FIG. 1, from a CPAP generator, with a CPAP pressure of 4 cm H₂O.
Figure 5:
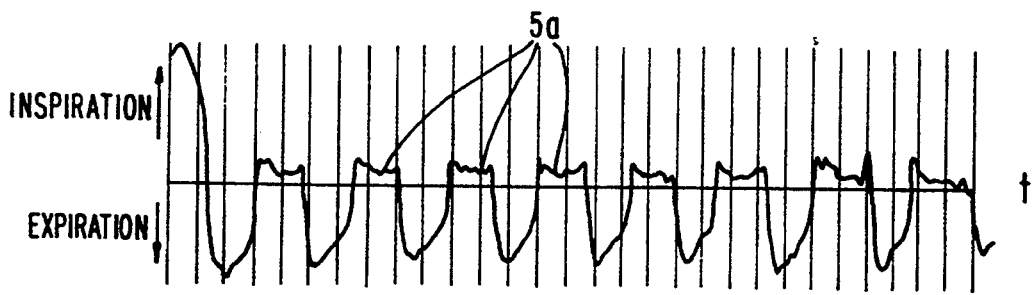
FIG. 5 is the waveform of the airflow of a 30 second epoch to the sleeping patient of FIG. 1, from a CPAP generator, with a CPAP pressure of 2 cm H₂O.

When the CPAP pressure was decreased to 8 cm H₂O, as illustrated in FIG. 2, a partial flattening of the inspiratory flow wave form, at regions 2a, began to occur. This flattening became more definite when the pressure was decreased to 6 cm H₂O, as illustrated by the reference numeral 3a in FIG. 3. The flattening becomes even more pronounced, as seen at the regions 4a of FIG. 4, when the pressure was reduced to 4 cm. Reductions in the CPAP pressure from the pressure of obstruction free respiration resulted in snoring by the patient. When the pressure was reduced to 2 cm H₂O, as illustrated in FIG. 5, there was virtually zero inspiratory flow during the inspiratory effort, as seen at the portions 5a. Shortly after the recording of the waveform of FIG. 5, the patient developed frank apnea and awakened.

The waveforms of FIGS. 1-5 illustrate that, as the pressure is lowered, a predictable index of increasing collapsibility of the airway occurs, prior to the occurrence of frank apnea, periodic breathing or arousal.

Figure 6:
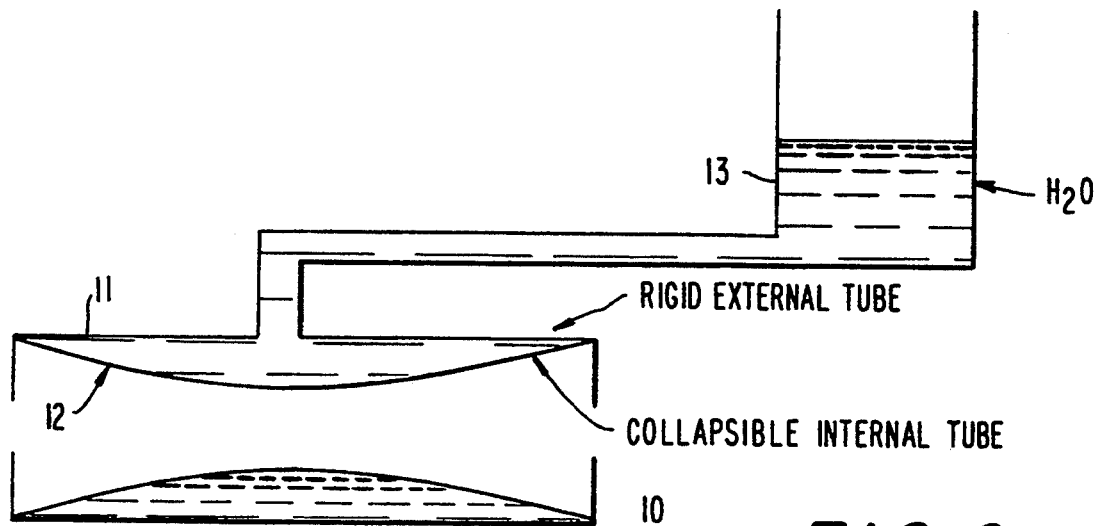
FIG. 6 is a simplified cross sectional view of a Starling resistor.
Figure 7:
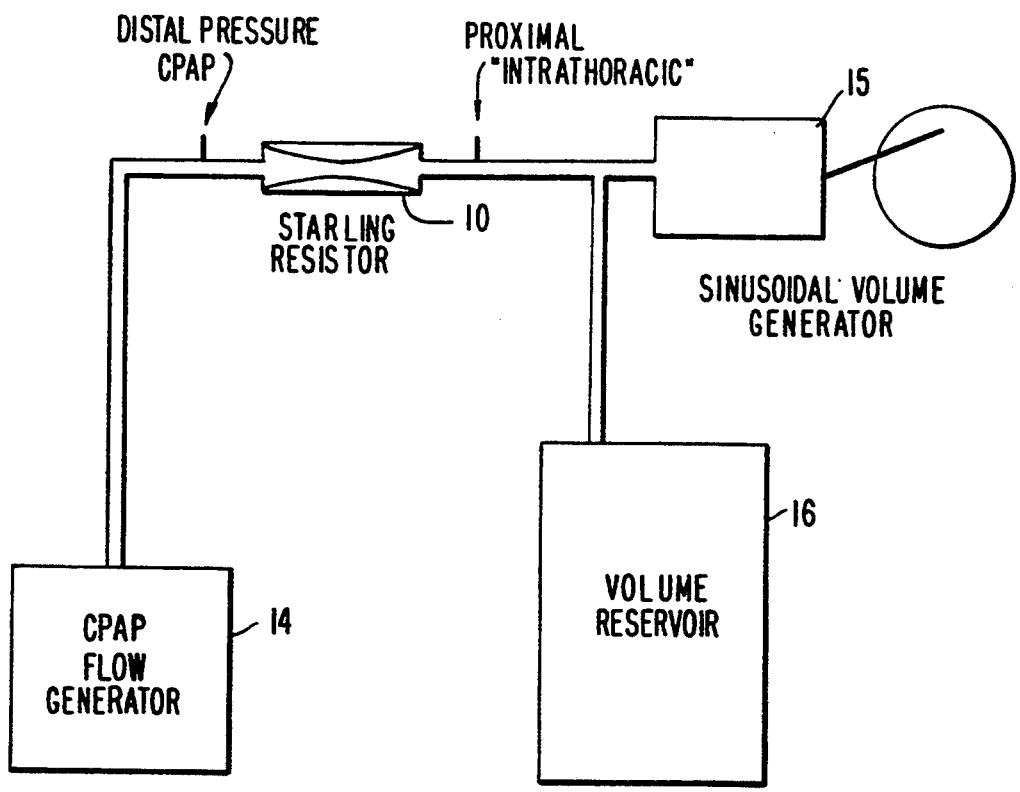
FIG. 7 is a simplified block diagram of an experimental setup employing a Starling resistor.

The waveforms of FIGS. 1-5 are consistent with experiments wherein the collapsible segment of the air passage is simulated by a Starling resistor. A Starling resistor 10, as illustrated in FIG. 6, is comprised of a rigid external tube 11 supporting an internal collapsible tube 12. Water is introduced into the space between the outer tube 11 and inner tube 12, for example via a tube, from a water column 13 of adjustable height, to enable variation of the external pressure applied to the collapsible tube 12. With reference to FIG. 7, in this experiment, a commercial CPAP flow generator 14 is coupled to the "distal" end of the Starling resistor 10, and "respiration" is simulated by a sinusoidal pump 15 coupled to the "proximal" or "intrathoracic" end of the resistor 10. A volume reservoir 16 is coupled to the proximal end of the Starling resistor, to provide a capacitive volume that prevents excessive negative pressure from developing during total system occlusion (apnea).

Figure 8:
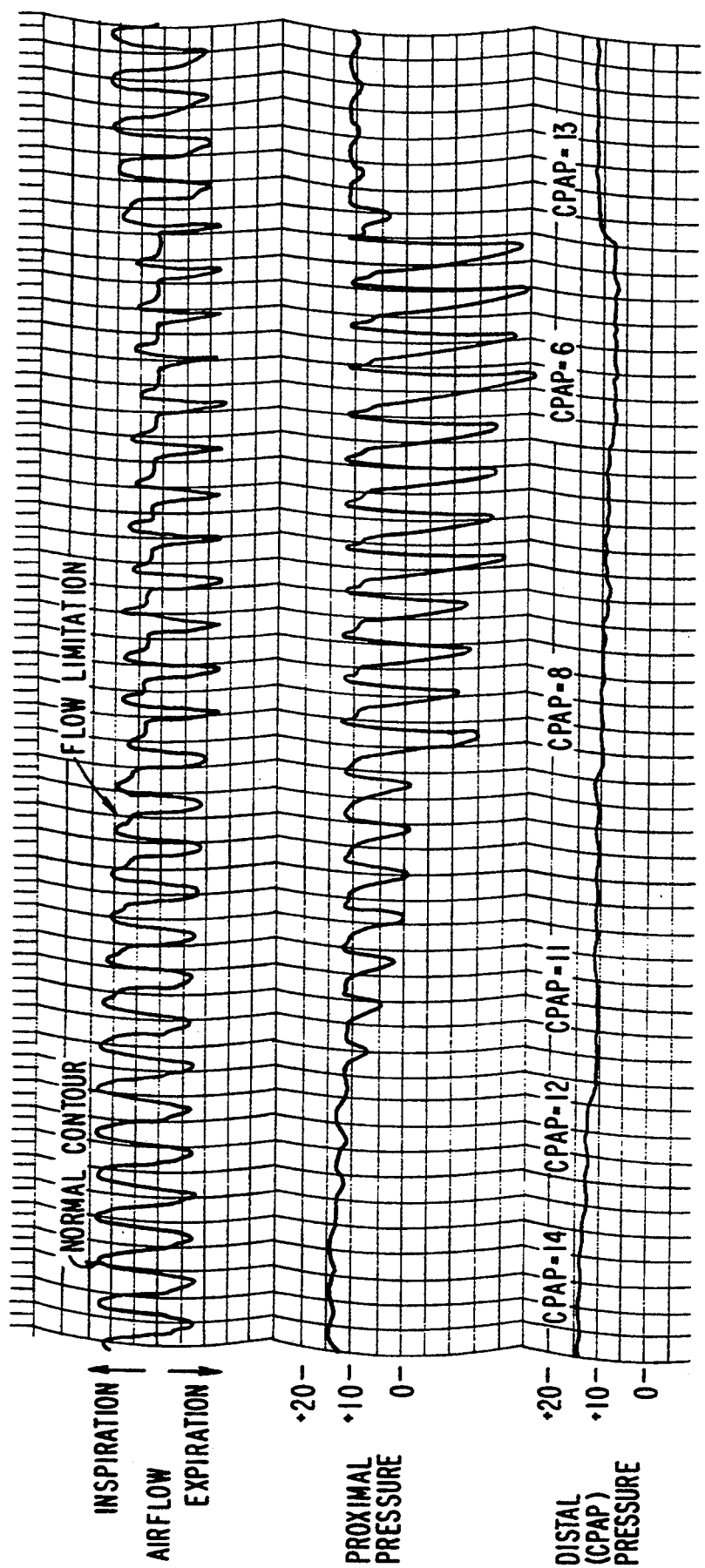
FIG. 8 is a set of waveforms generated by use of the setup of FIG. 7.

The flow tracing of FIG. 8 was generated using the system of FIG. 6, with the level of water in the column 13 set between 5 and 15 cm H₂O. The airflow from the CPAP flow generator was started at a pressure of 14 cm H₂O, then sequentially decreased to 12 cm, 11 cm, 8 cm and 6 cm H₂O, and finally returned to 13 cm H₂O. In this figure, the upper curve shows the waveform of the airflow, the middle curve shows the waveform of the proximal pressure (i.e. at the port of the sinusoidal generator 15, and the lower curve illustrates the CPAP pressure. The gradations at the top of FIG. 8 denote seconds. FIG. 8 thus reflects the large increase in resistance across the Starling resistor, and mimics the increasingly negative intrathoracic pressure routinely seen in patients with an apnea, snoring and any increased airway resistance syndrome.

In accordance with the invention, analysis of waveforms of the flow of air, of the type illustrated in FIGS. 1-5, is employed in order to control the flow of air from a CPAP generator, to thereby minimize the flow of air from the generator while still ensuring that flow limitation does not occur.

Figure 9:
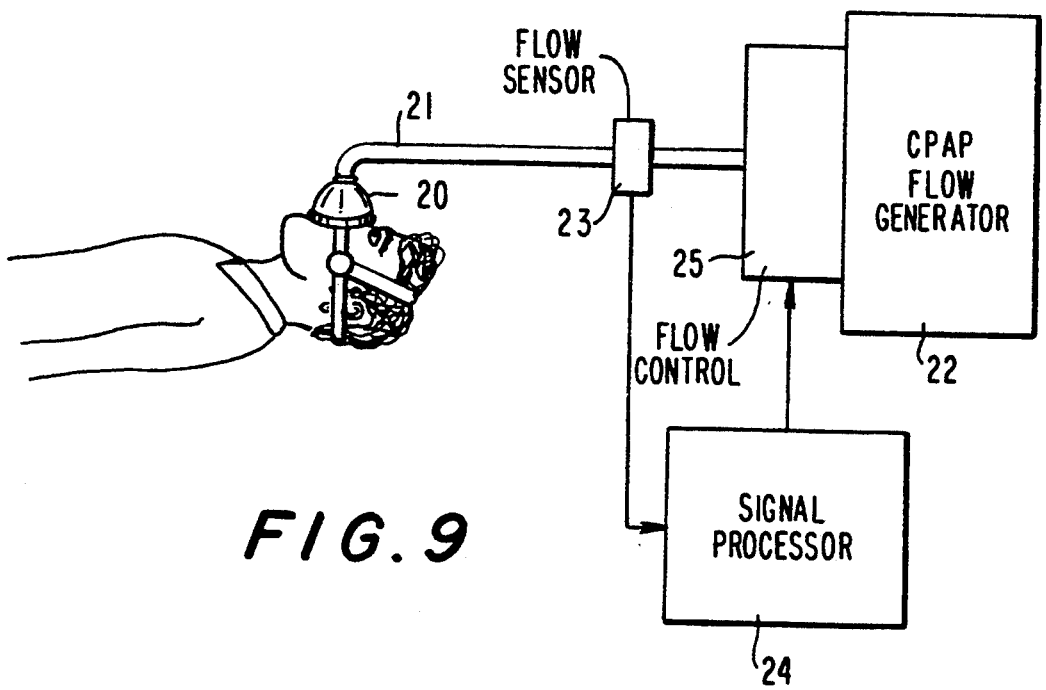
FIG. 9 is a simplified block diagram of a system in accordance with the invention.

In one embodiment of the invention, as illustrated in FIG. 9, a CPAP mask 20 is connected via tube 21 to receive air from a CPAP flow generator 22. These elements may be of the type disclosed in U.S. Pat. No. 5,065,756, although the invention is not limited thereto, and any conventional CPAP system may alternatively be employed. A conventional flow sensor 23 is coupled to the tube 21, to provide an electric output signal corresponding to the waveform of the airflow in the tube 21. This signal is applied to a signal processor 24, which detects the existence in the waveforms of conditions that indicate flow limitation. The signal processor 24 outputs a signal to a conventional flow control 25 for controlling the pressure applied by the flow generator to the tube 21. It is of course apparent that, depending upon the type of flow generator 22, the signal processor may directly control the flow generator, instead of controlling a flow control device 25.

Figure 10:
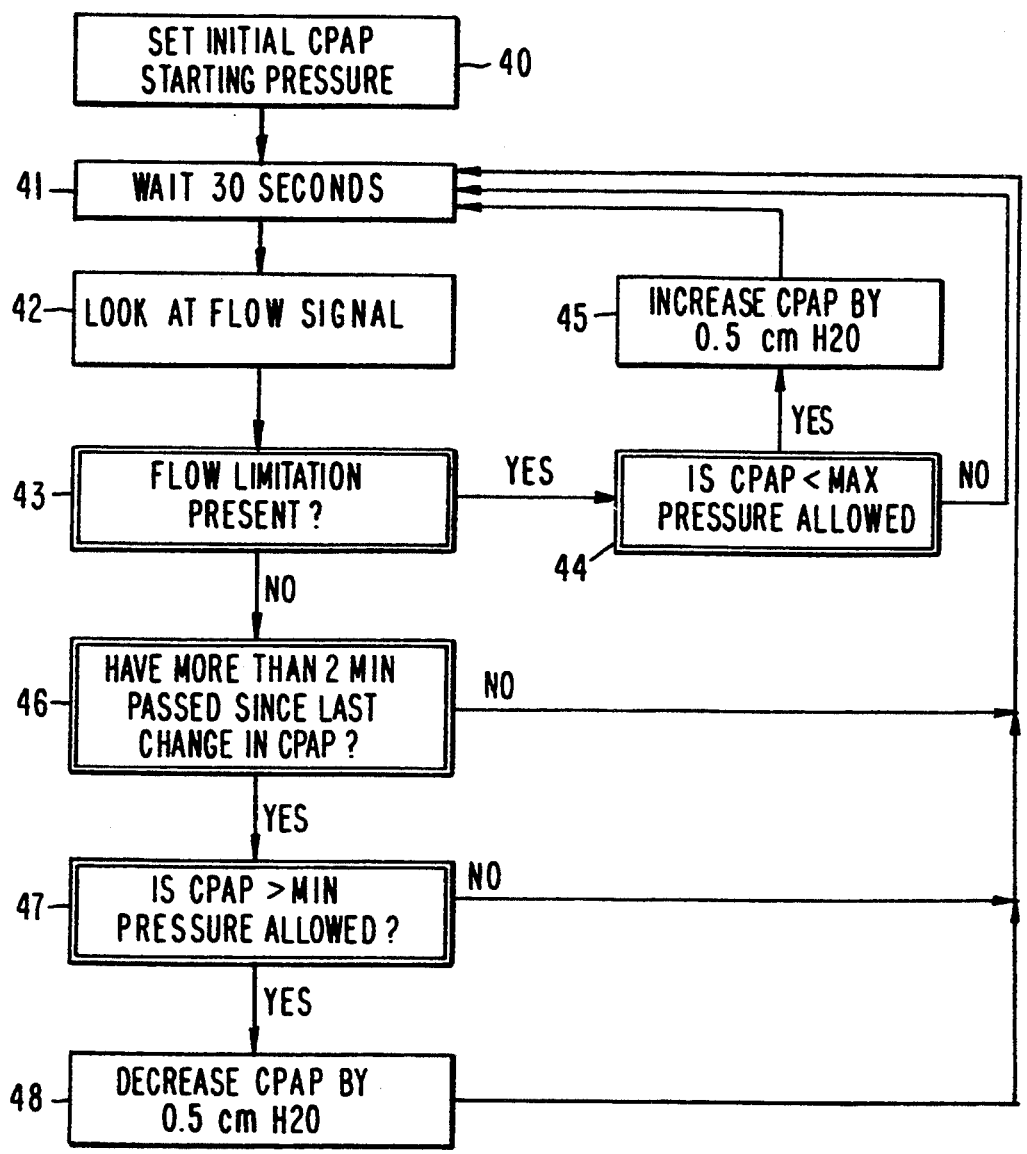
FIG. 10 is a flow diagram illustrating one technique for adjusting the CPAP pressure, in accordance with the invention.

One method for adjusting the CPAP pressure in accordance with the invention is illustrated in FIG. 10. After the CPAP mask has been fitted to a patient, and the CPAP generator has been connected to the mask, at step 40 the CPAP pressure is set at a starting pressure. This pressure is a pressure at which flow limitation for the patient does not occur. After a settling period of about 30 seconds, at step 41, the flow signal is analyzed, at step 42.

If it is determined in step 43, that flow limitation has occurred, and the CPAP pressure is less than the maximum allowed as determined at step 44, the CPAP pressure is increased by 0.5 cm H₂O, at step 45, and the procedure jumps back to the settling step 41 for further processing. If, at step 44, the pressure was not less than the maximum allowed CPAP pressure, the program jumps back to the settling step 41 without increasing the CPAP pressure.

If, at step 43, it was determined that a flow limitation was not present, then a determination is made, at step 46, if a predetermined time has elapsed following the last change in the CPAP pressure. The predetermined time may be, for example, two minutes. If the predetermined time has not elapsed, the program jumps back to the settling period of step 41. Otherwise, i.e. if the predetermined minimum time has elapsed, at step 47 it is determined whether or not the CPAP pressure is greater than the minimum allowed pressure. If it is greater than the minimum allowed pressure, then the CPAP pressure is decreased by 0.5 cm $H_2O$, at step 48, and the program jumps to the settling step 41. Otherwise, the program jumps back to the settling step 41 without decreasing the CPAP pressure.

While the above described example of the method of the invention employed CPAP pressure change steps of 0.5 cm $H_2O$, it is apparent that the invention is not limited to steps of this magnitude. In addition, the steps are not necessarily equal throughout the range of adjustment.

In step 43, as above discussed, it was determined if flow limitation was present or not. This step may involve any of a number of waveform analysis procedures. For example, several indices of flow limitation and/or partial airway obstruction which can be used, singly or in combination, include:

1. The derivative of the flow signal equals zero.
2. The second derivative between peaks of the flow signal is zero for a prolonged interval.
3. The ratio of early inspirational flow to midinspirational flow is less than or equal to 1.

The following events, which are not necessarily indications of flow limitation, but do indicate obstructions, in the waveform analysis, may also be employed in the determination of flow limitation:

1. Reduced slope of the line connecting the peak inspiratory flow to the peak expiratory flow.
2. Steep upward or downward stroke (dV/dt) of the flow signal.
3. Ratio of inspiratory flow to expiratory flow over 0.5.

Thus in accordance with the invention, indices of increased inspiratory effort may also be employed which are secondary to airway obstruction, in the face of which flow limitation becomes more likely. It is evident that analyses of this type may be effected by conventional hardware or software. The invention, however, is not limited to the above specific techniques for determining divergence of the waveform from the normal non-flow limited waveform to a waveform indicating the presence of flow limitation.

While the invention has been disclosed and described with reference to a limited number of embodiments, it will be apparent that variations and modification may be made therein, and it is therefore intended in the following claims to cover each such variation and modification as falls within the true spirit and scope of the invention.

What is claimed is:

1. A method for optimizing the positive airway pressure to a patient, comprising the steps of:
   a) applying an initial level of continuous positive airway pressure to a patient, which is then optimized by:
   b) continuously monitoring the inspiratory flow of air to the patient;
   c) defining an inspiratory waveform contour of said inspiratory flow for each breath;
   d) analyzing each said inspiratory waveform contour to determine the presence or absence of patient airway obstruction; and
   e) increasing said pressure when the contour of said waveform corresponding to inspiration indicates patient airway obstruction, and decreasing said pressure when said waveform corresponding to patient inspiration does not indicate patient airway obstruction.

2. The method of claim 1, wherein step e comprises increasing said pressure when the contour of said waveform corresponding to inspiration for a predetermined duration indicates patient airway obstruction, and decreasing said pressure when said waveform corresponding to patient inspiration for a predetermined duration does not indicate patient airway obstruction.

3. The method of claim 2, wherein said predetermined duration is sufficient to define a plurality of inspiratory waveform contours.

4. The method of claim 1, wherein said pressure is increased when the contour of said waveform corresponding to inspiration includes a plateau.

5. The method of claim 1, wherein said pressure is increased when a portion of the contour of said waveform corresponding to inspiration is flattened.

6. The method of claim 1, wherein said pressure is increased when the contour of said waveform corresponding to inspiration deviates from a substantially sinusoidal shape.

7. An apparatus for the treatment of patient airway obstruction, comprising an air source arranged for directing airflow to a patient and establishing an initial level of continuous positive airway pressure to the patient, a flow sensor to sense airflow to the patient, a signal processor operatively connected to said flow sensor for defining an inspiratory waveform contour of said airflow to the patient, and a controller operatively connected to said signal processor, wherein said signal processor further having means for determining the presence or absence of patient airway obstruction from said inspiratory waveform contour, and said controller having means for adjusting the pressure to the patient in response to the determination by said signal processor of the presence or absence of upper airway obstruction.

8. The apparatus of claim 7, wherein said controller further comprises means for increasing the pressure to the patient in response to a determination by said signal processor of the presence of patient airway obstruction for a predetermined duration, and said controller further having means for decreasing the pressure to the patient in response to a determination by said signal processor of the absence of patient airway obstruction for a predetermined duration.

9. The apparatus of claim 7, wherein said signal processor further comprises means for determining the presence of patient airway obstruction when the contour of said waveform corresponding to inspiration includes a plateau.

10. The apparatus of claim 7, wherein said signal processor further comprises means for determining the presence of patient airway obstruction when a portion of the contour of said waveform corresponding to inspiration is flattened.

11. The apparatus of claim 7, wherein said signal processor further comprises means for determining the presence of patient airway obstruction when the contour of said waveform corresponding to inspiration deviates from a substantially sinusoidal shape.

12. An apparatus for the treatment of obstructive sleep apnea, comprising:
- a source of air; means for directing an airflow from said source to a patient and establishing an initial level of continuous positive airway pressure to a patient;
- sensing means for sensing the airflow to the patient; means in operative relationship for defining an inspiratory waveform contour; and
- means responsive to the inspiratory waveform contour for adjusting said pressure to the patient.

13. The apparatus of claim 12, wherein said means responsive to the inspiratory waveform contour has means for increasing said pressure when said inspiratory waveform contour indicates patient airway obstruction, and for decreasing said pressure when said inspiratory waveform contour does not indicate patient airway obstruction.

* * * * *